US006836744B1

(12) United States Patent
Asphahani et al.

(10) Patent No.: US 6,836,744 B1
(45) Date of Patent: Dec. 28, 2004

(54) PORTABLE SYSTEM FOR ANALYZING HUMAN GAIT

(75) Inventors: Fareid A. Asphahani, 2433 Beverly Way, Ottawa, IL (US) 61350; Hwa C. Lee, Charlottesville, VA (US)

(73) Assignee: Fareid A. Asphahani, San Francisco, CA (US)

( * ) Notice: Subject to any disclaimer, the term of this patent is extended or adjusted under 35 U.S.C. 154(b) by 208 days.

(21) Appl. No.: 09/931,040

(22) Filed: Aug. 17, 2001

Related U.S. Application Data (60) Provisional application No. 60/226,011, filed on Aug. 18, 2000.

(51) Int. Cl.[7] .............................................. G01P 15/00
(52) U.S. Cl. ....................... 702/141; 73/510; 377/124.2
(58) Field of Search .............................. 702/47, 54–57, 702/98, 101, 122, 138, 141–147, 151, 153, 160, 173, 179; 73/510, 865.4; 36/11.5; 377/24.2; 49/428

(56) References Cited

U.S. PATENT DOCUMENTS

| | | | | |
|---|---|---|---|---|
| 5,372,365 A | * | 12/1994 | McTeigue et al. | 473/409 |
| 5,561,919 A | * | 10/1996 | Gill | 36/11.5 |
| 5,864,333 A | * | 1/1999 | O'Heir | 345/157 |
| 6,122,340 A | * | 9/2000 | Darley et al. | 377/24.2 |
| 6,122,846 A | * | 9/2000 | Gray et al. | 49/428 |
| 6,145,389 A | * | 11/2000 | Ebeling et al. | 73/865.4 |
| 6,301,964 B1 | * | 10/2001 | Fyfe et al. | 73/510 |
| 6,356,856 B1 | * | 3/2002 | Damen et al. | 702/160 |
| 2003/0009308 A1 | * | 1/2003 | Kirtley | 702/141 |

OTHER PUBLICATIONS

60/213,981, filed Jun. 24, 2000, Kirtley.*

* cited by examiner

*Primary Examiner*—Marc S. Hoff
*Assistant Examiner*—Mohamed Charioui
(74) *Attorney, Agent, or Firm*—Krieg DeVault Lundy LLP (57) ABSTRACT

The invention is a portable gait analyzer comprising of at least one independent rear foot motion collection unit, at least one independent lower shank motion collection unit, plantar pressure collection unit, at least one processing and display unit, and a soft casing unit. A plurality of accelerometers, rate sensors, force sensor resistors, and pressure sensors provide for the acquisition of acceleration signals, angular velocity signals, foot force signals, and foot pressure signals to be processed. At least one central processing unit, a plurality of memory components, input/output components and ports, telemetry components, calibration components, liquid crystal displays components for the processing and outputting of three dimensional acceleration, angular velocity, tilt, and position. The rearfoot motion collection unit and lower shank motion collection unit interact with the processing and display unit to calculate rear foot kinematic data crucial to identify the motions of pronation and supination. The plantar pressure collection unit interacts with the processing and display unit to calculate plantar pressure data crucial to identify the center of pressure line and excessive and abnormal loads on the sole of the foot. These factors of rear-foot kinematics and plantar pressure lead to gait style identification.

41 Claims, 7 Drawing Sheets

PORTABLE SYSTEM FOR ANALYZING HUMAN GAIT

This invention claims priority of provisional patent application 60/226,011 filed Aug. 18, 2000, and is incorporated by reference herein.

FIELD OF THE INVENTION

This invention relates to a portable system for analyzing human gait. More particularly, this invention relates to foot mounted sensors comprising a detachable plantar pressure collection unit, a detachable motion tracking unit, a detachable processing and display unit, a detachable sole unit, a soft foot casing unit, and a shank cover.

DESCRIPTION OF THE PRIOR ART

U.S. Pat. No. 5,899,963 entitled: System and Method for Measuring Movement of Objects, discloses a device that measures the distance traveled, speed and height jumped while a person is running or walking. An electronic circuit performs mathematical calculations to determine distance and height. A microprocessor calculates an output speed based upon step-distance and elasped time, and the distance traveled from the sum of all previous steps. A display shows the distance traveled, speed or height jumped.

U.S. Pat. No. 5,875,571 entitled: Insole Pad having a Step-Counting Device, includes an insole pad body, a fluid bag, a connecting portion, a pressure-sensitive sensor, a thermostat, a transmitting circuit, and a receiving circuit. Variation in pressure and temperature signals are detected, and converted to values, which are transmitted by an RF signal, and displayed on a liquid crystal display.

U.S. Pat. No. 4,745,930 entitled Force Sensing Insole for an Electro-Goniometer, is used for analyzing the gait of a patient. The insole comprises three separate chambers, which each contain contact switches. A plurality of parallel fingers are provided on the inwardly facing surface of the chambers, and extend to a terminal at the end of the strip.

U.S. Pat. No. 3,974,491, entitled: Load Signaling Device for a Patient's Foot, discloses a foot pad sized to substantially cover the inner sole of a shoe. A resilient liquid filled tube is positioned within the foot pad. A pressure responsive means in communication with the liquid actuates a signal means at a predetermined pressure of said liquid.

U.S. Pat. No. 3,791,375, entitled: Device for Sensing and Warning of Excessive Ambulation Force, discloses a fluid containing load cell which deflects and changes its volume in accordance with the amount of load thereon. An alarm indicates when a predetermined load on the cell is reached.

U.S. Pat. No. 4,647,918, entitled: Multi-event Notification System for Monitoring Critical Pressure Points on Persons with Diminished Sensation of the Feet, discloses a plurality of pressure transducers for measuring and monitoring pressure, are connected to a microprocessor, which is programmable to monitor pressure over a pre-selected time interval. An alarm indicator is actuated when the total number of pressure events exceed the threshold limit.

U.S. Pat. No. 4,703,445, entitled: Atheletic Shoe for Running Disciplines and a Process for Providing Information and/or for Exchanging Information Concerning Moving Sequences in Running Disciplines, discloses a process for gathering information comprising at least one sensor located in the sole, to emit at least one output signal which is transmitted to a remote receiver linked to a computer. The computer determines the distance between the first and second shoes, based upon the delay of the emissions, as well as other characteristic values related to stride rate and length of stride.

U.S. Pat. No. 5,929,332, entitled: Sensor Shoe for Monitoring the Condition of a Foot, discloses a sensor shoe having a base, a foot receiving portion extending from the base, and an inner sole positioned within the foot receiving portion and atop the base. Sensors in the inner sole generate signals to determine if a critical situation exists. A microcomputer releases medication when a critical situation exists.

U.S. Pat. No. 5,583,776, entitled: Dead Reckoning Navigational System using Accelerometer to Measure Foot Impacts, integrates GPS data, dead reckoning sensors, and digital maps into a low cost, self-contained navigation instrument having a built-in radio frequency transponder, enabling individual positions to be monitored by a central coordinating facility.

U.S. Pat. No. 5,485,402, entitled: Gait Activity Monitor, to determine and record the number of steps taken by a wearer during selected intervals. An optical transmitter receive permits the monitor to be optically coupled to a computer for transmitting data. The duration of the selected time interval can be changed, and the gait activity data stored and downloaded for analyzing the data and for generating selected reports.

U.S. Pat. No. 6,010,465, entitled: Apparatus and Method for Characterizing Gait, discloses a treadmill having multiple transducers to identify the occurrence of heel-strike and toe-off movements while walking or running. A computer identifies two non-contiguous groups of transducers measuring a force greater than zero, and calculates the forces exerted by each foot.

Also noted of interest is an article by Jacqueline Wertsch, MD, John Webster PhD, and Willis Tompkins PhD, published in the Journal of Rehabilitation Research and Development, Vol. 29, No. 1, Published in 1992 on pages 13 through 18, a copy of which will be supplied.

BACKGROUND

Human gait, the manner of walking and running, is influenced by a number of factors that include foot structure, physical characteristics, muscle action, ground reaction forces, joint kinematics, and the presence of shoes and their structure. Determination and monitoring of human gait is important in athletic activity, medical diagnosis, and normal human motion and movement, particularly since injuries to the lower extremities during walking or running depend on extrinsic factors such as velocity, frequency of walking or running over time, equipment, and terrain. A method for performing this quickly, accurately, and inexpensively would clearly be beneficial. The device described here provides an effective method for measuring and analyzing human gait and identifying human gait style.

Over the past ten years, studies have shown that shoes can significantly contribute to injuries of the lower extremities, especially when shoe structure is not properly matched to foot dynamics. Pronation and supination have been shown to be substantially influenced by the shoe, wherein shoe structure differences affect the amount of eversion and inversion in the rearfoot. Excessive pronation (over-pronation) is associated with too much movement of the rear-foot during the stance phase of gait, and elevated peak plantar pressure is associated with excessive and abnormal loads on the foot. Both of these factors have been associated with injuries of the lower extremities. The device described here measures foot dynamics both barefoot and inside shoes to provide rear-foot motion analysis, plantar pressure analysis, and gait style analysis, which can assist footwear consumers in proper shoe selection.

Although the embodiment of the present invention applies to a device that measures and analyzes human gait and identifies gait style, the device may be used to measure key factors important in athletic training and sports medicine. This device may also find use in other biomedical and pediatric applications such as orthopedic diagnosis and rehabilitation. The device can be used to measure three dimensional foot and shank acceleration, angular velocity, and position, by calculating the tilt of the independent foot and independent shank, the rearfoot motion angles of inversion/eversion, adduction/abduction, dorsiflexion/plantar flexion, stride length, pace, maximum plantar pressure, mean plantar pressure, and center of pressure gait-line.

BRIEF SUMMARY OF INVENTION

The invention is a portable gait analyzer comprising of at least one independent rear foot motion collection unit, at least one independent lower shank motion collection unit, plantar pressure collection unit, at least one processing and display unit, and soft casing unit. The invention comprises a plurality of accelerometers, rate sensors, force sensor resistors, and pressure sensor components for the acquisition of acceleration signals, angular velocity signals, foot force signals, and foot pressure signals to be processed. The invention comprises at least one central processing unit, a plurality of memory components, input/output components and ports, telemetry components, calibration components, liquid crystal displays components for the processing and outputting of three dimensional acceleration, angular velocity, tilt, and position. The rearfoot motion collection unit and lower shank motion collection unit interact with the processing and display unit to calculate rear foot kinematic data crucial to identify the motions of pronation and supination. The plantar pressure collection unit interacts with the processing and display unit to calculate plantar pressure data crucial to identify the center of pressure line and excessive and abnormal loads on the sole of the foot. These factors of rear-foot kinematics and plantar pressure lead to gait style identification.

These and other objects and advantages of the present invention will be more readily apparent from the following detailed description of the preferred embodiment of the invention, when read in conjunction with the accompanying drawings.

DESCRIPTION OF THE PREFERRED EMBODIMENT OF THE INVENTION

This invention can be applied to all sports medicine rehabilitation and training including running, jogging, basketball, skiing, skating, football, baseball, ice hockey, hockey, tennis, golf, high jump, weight lifting, and broad jump. Special uses including portable scales for measuring body weight and mass Additionally, other applications include biomedical and podiatric uses such as orthopedic diagnosis and rehabilitation.

Current methods of gait analysis include expensive clinical devices such as the Vicon, EMED, and Pedar costing up to hundreds of thousands of dollars. Also, these devices are not portable.

The preferred embodiment of the present invention, as shown in FIG. 1 through FIG. 11, discloses a portable apparatus 10 for analyzing human gait comprising one or more external measuring devices 42, such as one or more selectively positioned motion tracking units 20, 24 or a plantar pressure collection unit 30 (PPC) having a detachable insole 32 fitted with a plurality of sensors 34 between the plantar side of the foot 12 and the sole 15 of the foot. The apparatus 10 is releasably secured about a user's foot during operation thereof.

Figure 1:
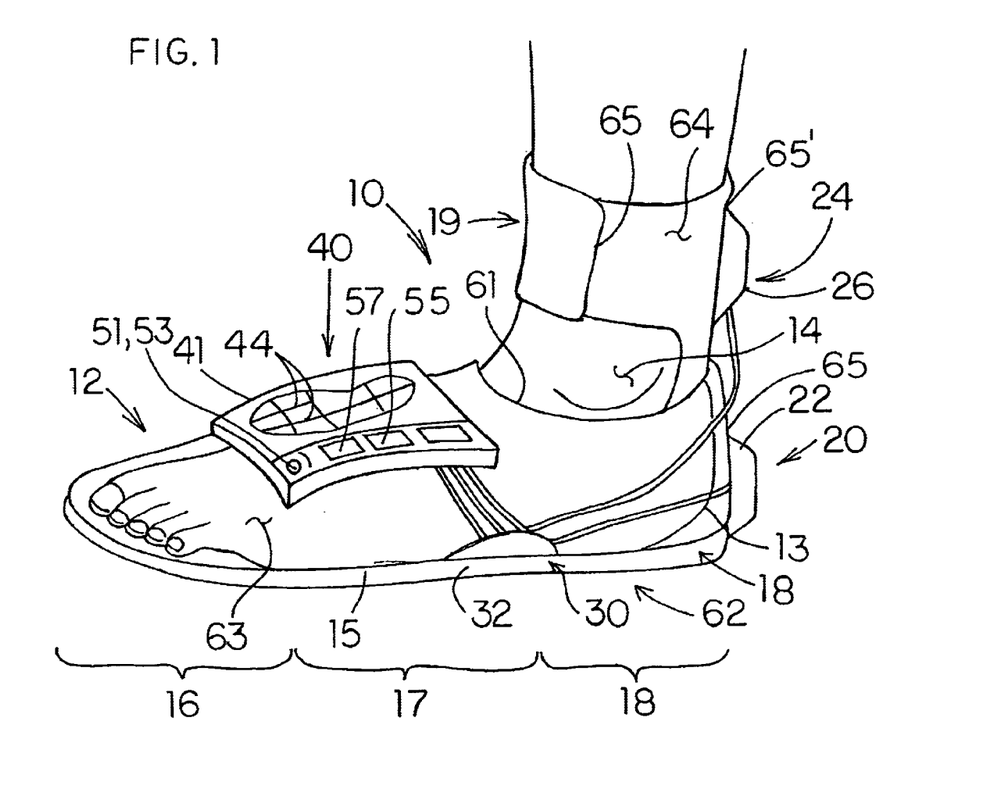
FIG. 1 is a perspective view of the overall human gait analysis device positioned on a user's foot.
Figure 2:
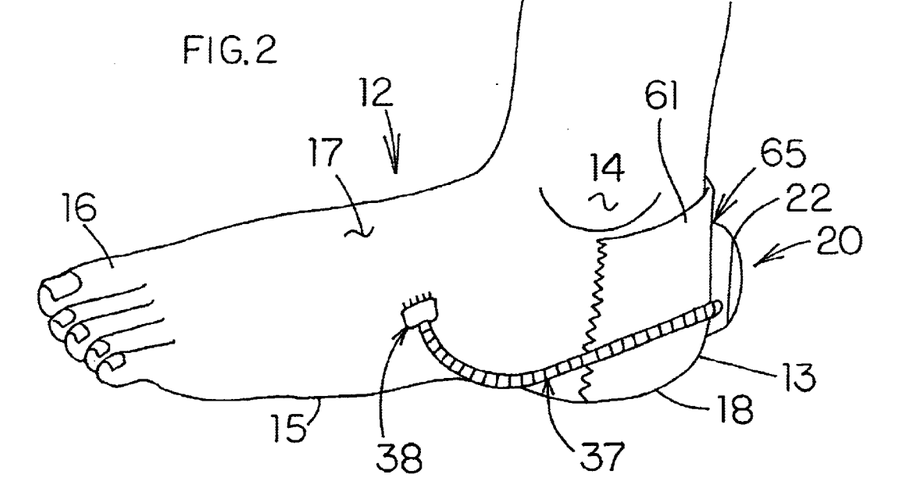
FIG. 2 is a breakaway detail view of the independent rearfoot motion collection unit shown in FIG. 1.
Figure 3:
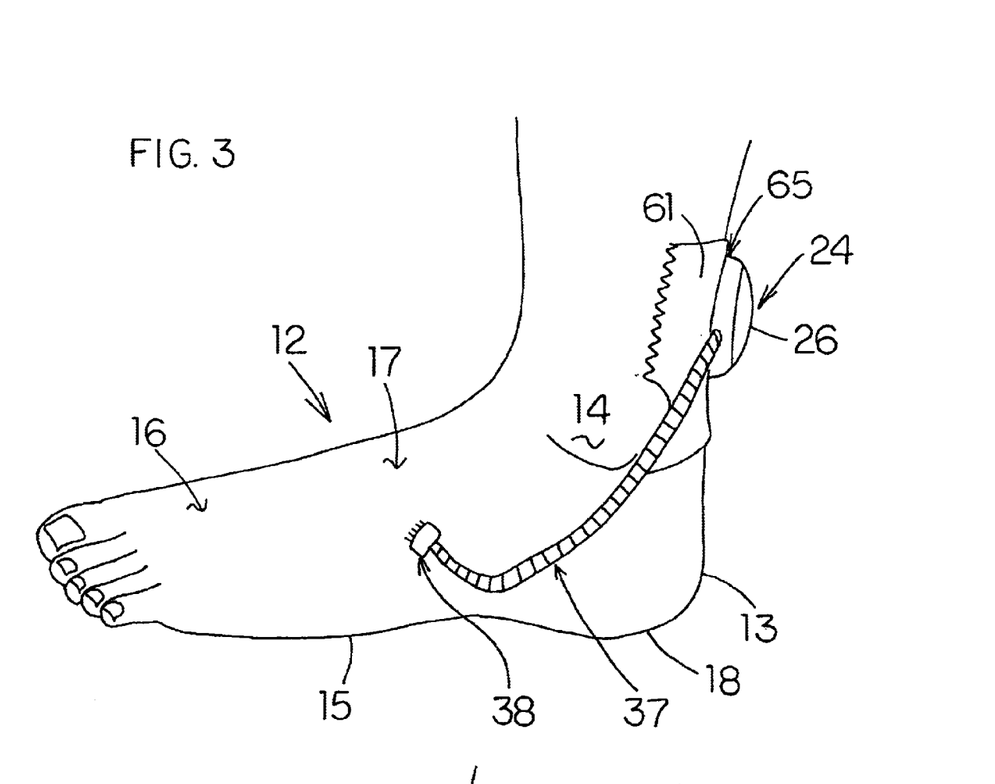
FIG. 3 is a breakaway detail view of the independent lower shank motion collection unit shown in FIG. 1.

As shown in FIG. 1 and in further detail in FIG. 2, a first detachable motion tracking unit 20 is located at the rear of the foot 12 in proximity to the heel 13, at a location above the ankle 14. The first detachable motion tracking unit 20 includes a rearfoot motion collection and rate sensing unit 22 (FMC). As shown in FIG. 1 and FIG. 3, a second detachable motion tracking unit 24 is located at the rear of the foot 12 above the ankle 14. The second detachable motion tracking unit 24 includes a lower shank motion collection and rate sensing unit 26 (SMC).

A key component in determining the gait of a specific individual depends on the movement of the rearfoot 18 and the lower shank 19 areas. Independent motion measurement units 22, 26 are placed on the rear-foot 18 and the lower shank 19, respectively, of the left and/or right foot. The units 22, 26 contain accelerometers 85, 95 and rate sensors 87, 97 to measure the specific motion of the rearfoot 18 and lower shank 19, respectively. When in conjunction with each other, the units 22, 26 can calculate the specific motion based on the data collected, the three-dimensional static and dynamic acceleration, angular velocity of the rearfoot 18 and the lower shank 19. The accelerometers 85, 95 each provide 2-axis tilt information, measuring both the static (gravity) and dynamic (body motion) movements.

Figure 4:
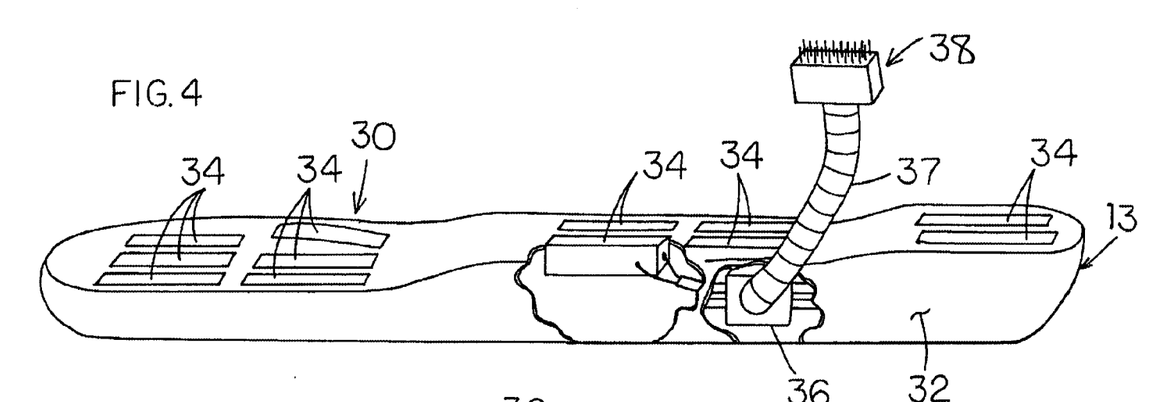
FIG. 4 is a breakaway detail view of the plantar pressure collection unit, shown in FIG. 1.
Figure 7:
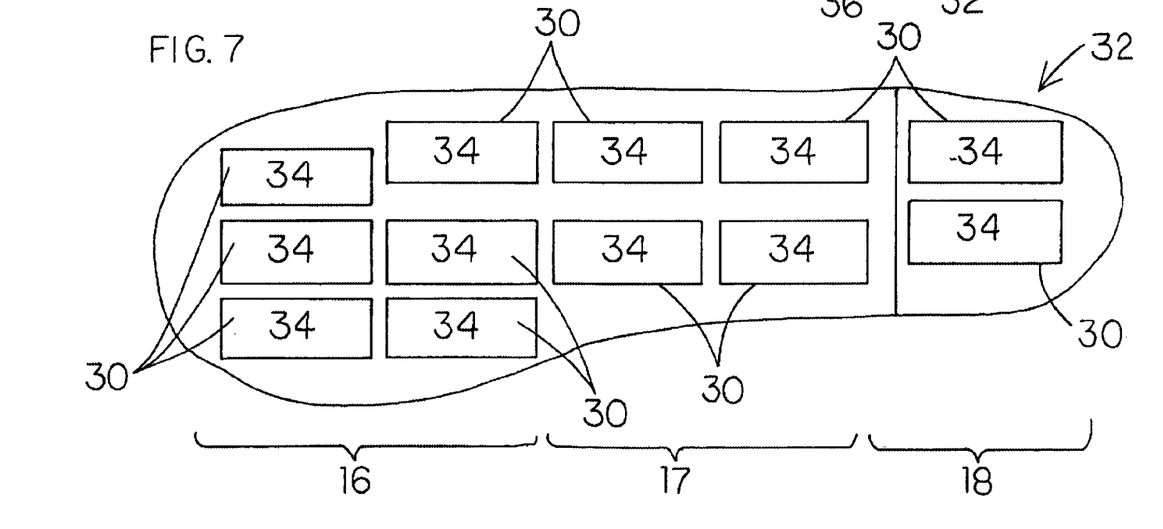
FIG. 7 is a detail view of the pressure sensor/FSR placement of the plantar pressure collection unit, in the forefoot, midfoot and rearfoot of the insole, shown in FIG. 1.

The plantar pressure collection unit 30, comprises force sensor resistors and pressure sensors 34, which are placed within insole 32 and located along the $1^{st}$ phalange, $2^{nd}$ phalange, and $3^{rd}$ and $4^{th}$ phalanges in the forefoot 16, along the $1^{st}$ metatarsal head, $2^{nd}$ metatarsal head, and $4^{th}$ metatarsal head in the forefoot 16, along the 1$^{st}$ metatarsal base and 4$^{th}$ and 5$^{th}$ metatarsal bases in the midfoot 17, underneath the distal portion of the medial and lateral sides of the calcaneus in the midfoot 17, and at the medial and lateral surfaces of the calcaneus in the rearfoot 18. Such configuration of the force sensor resistors and pressure sensors 34 allows for an accurate measurement of the plantar pressure distribution. Specifically, the maximum pressure, location of the maximum pressure, mean pressure, and the pressure line can be determined. The layers on the insole 32 are flexible, electrically insulating, thin, and have resilient properties. The insole 32 is disposable and replaceable. The insole 32 is preferably made to selectively fit all shoe sizes.

FIG. 4 is a detailed perspective view of the plantar pressure collection unit 30, showing an insole 32, which is preferably flexible, durable, electrically insulating, and resilient. Pressure sensors (FSR) 34 are specifically placed about the forefoot 16, midfoot 17 and rearfoot 18 of the insole 32. FIG. 7 is a top view of the insole 32, shown in FIG. 4. The pressure sensors 34 are connected to a wire collection site 36. Protected output wires 37 extend from the wire collection site 36 to output pins 38, for connection to the processing and display unit 40.

Figure 5:
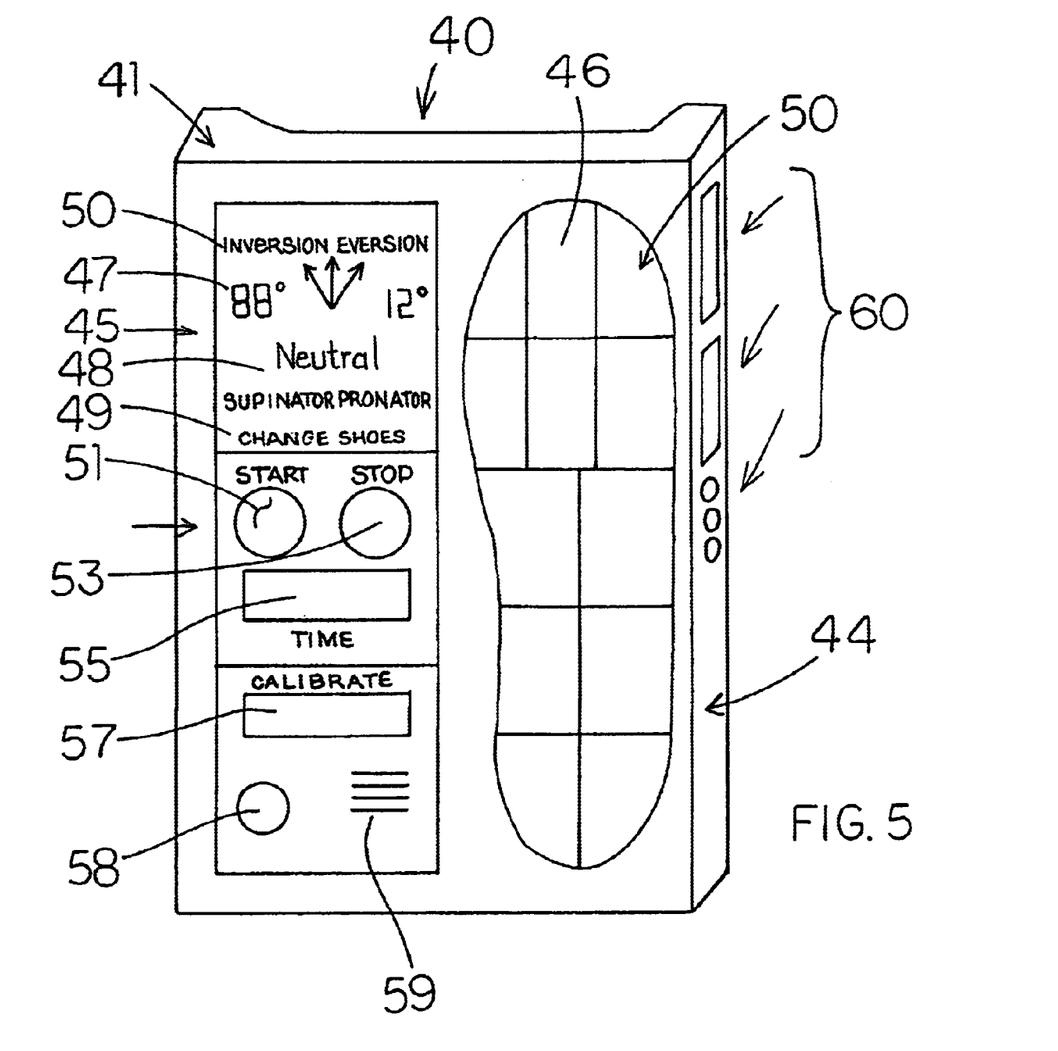
FIG. 5 is a detail view of the processing and display unit shown in FIG. 1.

In the processing and display unit 40, a central processing unit (CPU) 44 controls all data input from the rearfoot motion control unit 22, the lower shank motion control unit 26, and the plantar pressure collection unit 30. The data is processed by the CPU 44 for visual display and storage. On the processing and display unit 40, the vital gait information concerning the foot 12 from which the data is collected is displayed for the user to review. The information displayed comprises of the amount of eversion/inversion angle, gait identification (over-pronate, supinate, neutral), and the plantar pressure distribution in the form of a color coded mapping strategy where the data is normalized from the body weight calibration. The user can input commands to the processing and display unit 40 by indicating the start/stop 51, 53 of the data measurement cycle and perform static calibration.

FIG. 5 is a top view of the processing and display unit 40 shown in FIG. 1. The processing and display unit 40 comprises a casing 41, with a plurality of electrical components inside, including CPU 44. A visual display on processing and display unit 40 is preferably a LCD color display 50 in the shape of the sole of a foot 12, which displays plantar pressure at 46 and gait line data at 45.

Rearfoot motion angel 47, gait style identifier 48 and shoe-life evaluator at 49 are each displayed via the visual display of the processing and display unit 40. Measurement cycle buttons and elapsed time are shown as start 51, stop 53 and elapsed time display shown at 55. A calibration button 57, LED 58 and buzzer 59 are also preferably provided. One or more input/output ports 60 connect to external measuring devices 42, including the PPC unit 30. FMC unit 22 and SMC unit 26.

Figure 6:
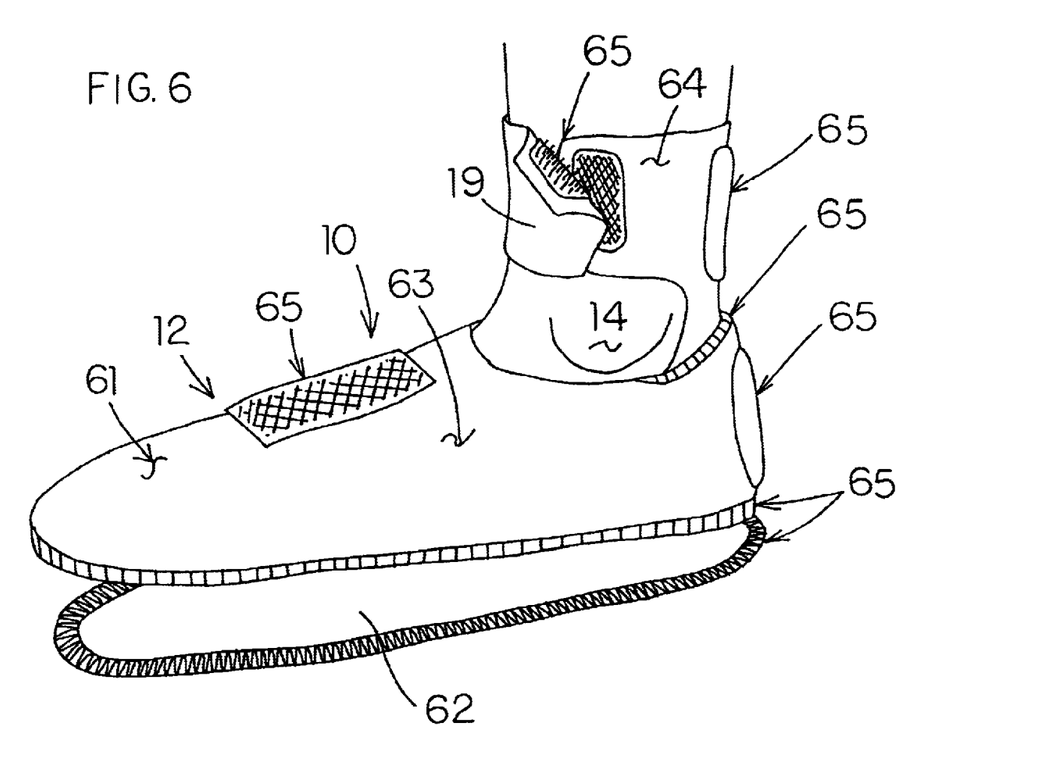
FIG. 6 is a detail view of the soft casing unit shown in FIG. 1.

A soft casing unit 61 is comprised of detachable parts known as the foot cover 63, the shank cover 64, and the sole cover 62, where the rearfoot motion collection unit 22, the lower shank motion collection unit 26 and the processing and display unit 40 are attached by a releasable securement means 65, such as a zipper, or hook and loop type fastening means. The soft casing unit 61 is preferably made to be selectively worn with or without shoes. All components are detachable, replaceable and function independent of each other.

FIG. 6 is a detailed view of the soft casing unit 61, comprising a detachable sole cover 62, a detachable foot cover 63, a detachable shank cover 64, a releasable securement means 65, such as a hook and loop fastener, are provided for detachable sole foot cover 63 and shank cover 64 connectors. Likewise the releasable securement means 65 provides for shank cover adjustment above the user's ankle 14.

FIG. 7 is a top view of the force sensor resistors and pressure sensors 34 placement in the PPC unit 30, shown in FIG. 4.

Figure 8:
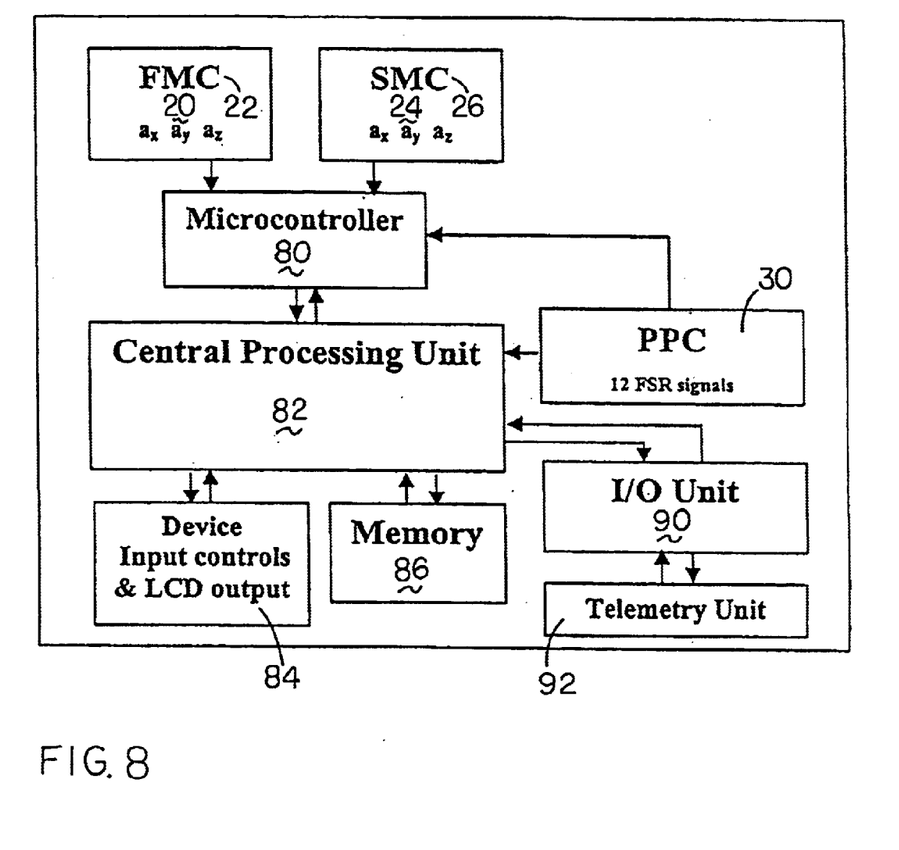
FIG. 8 is a Block diagram of processing method used in the human gait analysis device of the present invention.

FIG. 8 is a block diagram of the processing method, showing the FMC unit 22 of motion tracking unit 20 in one way electrical communication with a micro-controller 80. Likewise, the SMC unit 26 of motion tracking unit 24 is also in one way electrical communication with the micro-controller 80. A central processing unit 44 of the processing and display unit 40 is in two way electrical communication with the micro-controller 80. A PPC unit 30 directs signals from the force sensor resistors and pressure sensors 34 to the central processing unit 82 and to the micro-controller 80. Device input controls and LCD output 84 are in two way electrical communication with the central processing unit 82. Memory 86 is also in two way electrical communication with the central processing unit 82. An I/O unit 90 is also in two way communication with the central processing unit 82. A telemetry unit 92 is in two way communication with the I/O unit 90.

Figure 9:
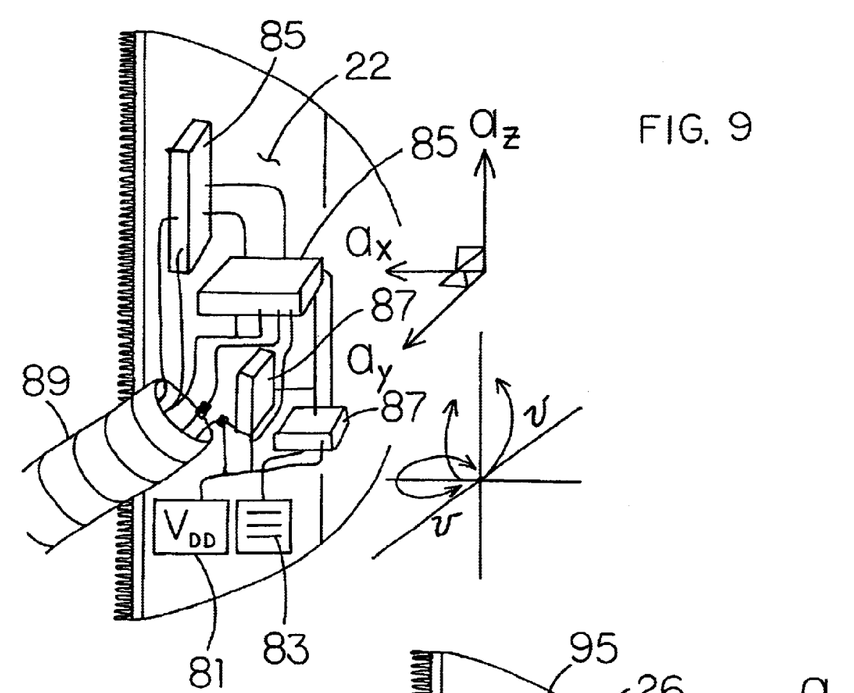
FIG. 9 is an inside view of the FMC showing the relationship of the power supply, common ground, plurality of accelerometers for 3D acceleration, plurality of rate sensor for multi-directional angular velocity, and output lines.

FIG. 9 is a pictorial inside view of the FMC unit 22. The FMC unit 22 includes a power supply 81, a common ground 83, a plurality of accelerometers 85 for 3D acceleration, a plurality of rate sensors 87 for multi-directional angular velocity, and output lines 89.

Figure 10:
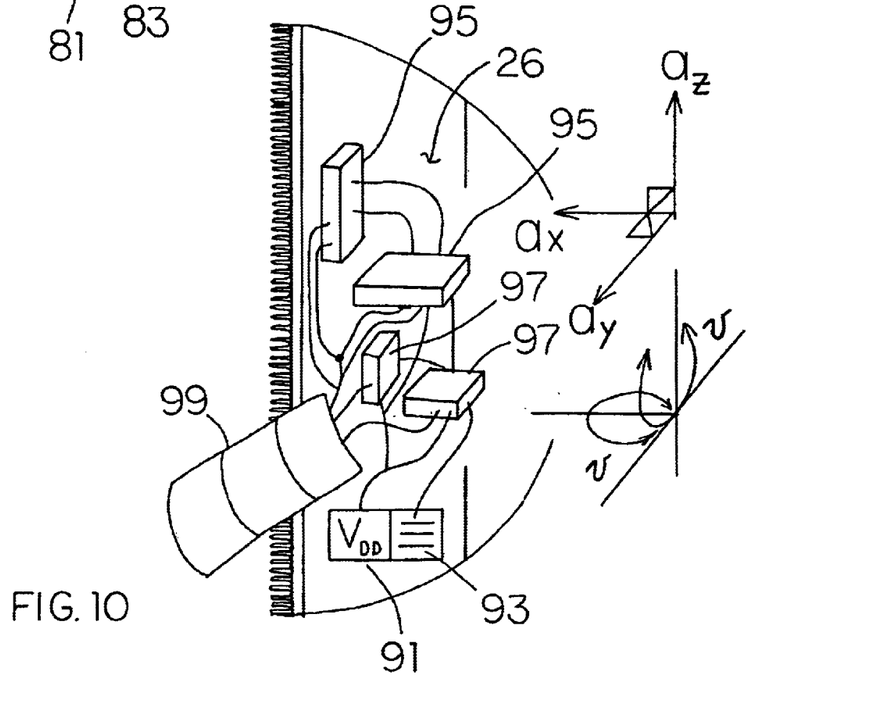
FIG. 10 is a detail view of the inside of the SMC, showing the relationship of the power supply, common ground, plurality of accelerometers for 3D acceleration, the plurality of rate sensors for multi-directional angular velocity, and the output lines.

FIG. 10 is a pictorial inside view of the SMC unit 26. The SMC unit 26 includes a power supply 91, a common ground 93, a plurality of accelerometers 95 for 3D acceleration, a plurality of rate sensors 97 for multi-directional angular velocity, and output lines 99.

This invention is novel and improves on the current methods of gait analysis for the following reasons:
1. It is portable.
2. It is light weight.
3. It is inexpensive.
4. It has functionally independent and detachable components.
5. It can be worn with or without shoes.
6. It has replaceable components.
7. It performs gait analysis on the feet and shoes independent of each other.
8. It can be hot sinkable to external devices including a PC, PDA, VCR, DVD player, TV, Projector unit, stereo, walkman, and CD player.

The invention being thus described, it will be evident that this invention may be varied in many ways, and such variations are not to be regarded as a departure from the spirit and scope of the invention. All such modifications and adaptations are intended to be included within the scope of this disclosure, and the following claims.

We claim:
1. A portable human gait analysis apparatus for releasable securement about a user's foot, wherein the apparatus comprises:
   a) a detachable sole;
   b) a soft casing unit having a detachable sole cover, a detachable foot cover, a detachable shank cover, and a releasable securement means for releasably and adjustably securing the detachable sole cover, the detachable foot cover, and the detachable shank cover about said user's foot;

c) a plantar pressure collecting unit positioned between a plantar side of said user's foot and the detachable sole;

d) a rearfoot motion collection unit having at least one accelerometer sensor and at least one rate sensor;

e) a lower shank motion collection unit having at least one accelerometer sensor and at least one rate sensor;

f) a detachable processing unit in electrical communication with the plantar pressure collection unit, the rearfoot motion collection unit, and the lower shank motion collection unit, said detachable processing unit for processing data from a plurality of said accelerometers and said sensors; and g) a visual display unit in electrical communication with the detachable processing unit for displaying the data processed by the processing unit.

2. The portable human gait analysis apparatus of claim 1, wherein the data from the central processing unit passes through an I/O unit to a telemetry unit for transfer to at least one of a PC and PDA, for storage and further analysis.

3. The portable human gait analysis apparatus of claim 2, wherein the data from the telemetry unit is transferred to at least one of: a walkman, a TV, a VCR, a DVD player, a CD player, a projection unit, a game console, a stereo and an internet site for entertainment purposes.

4. The portable human gait analysis apparatus of claim 1, wherein said soft casing unit is sized to fit within a user's shoe, with the rearfoot motion collection unit, the lower shank motion unit, and the processing and display unit attached to the outer portion of the user's shoe.

5. The portable human gait analysis apparatus of claim 1, wherein independent measurements are taken for said user's right foot and left foot, and said processing and display units function independently of each foot.

6. The portable human gait analysis apparatus of claim 1, wherein past data is stored in memory, and processed by the central processing unit for comparison between use.

7. The portable human gait analysis apparatus of claim 1, wherein the display unit is LCD display unit.

8. The portable human gait analysis apparatus of claim 1, wherein the central processing unit processes data from the plurality of accelerometers and sensors to determine pronation, supination and normal data based upon data received from the rearfoot motion collection unit and lower shank motion collection unit.

9. The portable human gait analysis apparatus of claim 1, wherein a user's body weight is calibrated by the central processing unit to provide a baseline for processing data.

10. The portable human gait analysis apparatus of claim 1, wherein the detachable sole is flexible, durable, electrically insulating, and resilient.

11. A portable human gait analysis apparatus for releasable securement about a user's foot, wherein the apparatus comprises:

a) a detachable sole which is flexible, durable, electrically insulating, and resilient;

b) a soft casing unit having a detachable sole cover, a detachable foot cover, a detachable shank cover, and a releasable securement means for releasably and adjustably securing the detachable sole cover, the detachable foot cover, and the detachable shank cover about said user's foot;

c) a plantar pressure collection unit positioned between a plantar side of said users foot and the detachable sole, to identify the center of pressure line and excessive and abnormal loads on the sole of the foot;

d) a rearfoot motion collection unit having at least one accelerometer sensor and a plurality of rate sensors to calculate rearfoot kinematic data crucial to identify the motions of pronation and supination;

e) a lower shank motion collection unit having at least one accelerometer sensor and a plurality of rate sensors to provide lower shank motion data, which when combined with data from the rearfoot kinematic data, to provide three dimensional static and dynamic acceleration, angular velocity, two-axis tilt information, and static and dynamic foot movements;

f) a detachable processing unit in electrical communication with the plantar pressure collection unit, the rearfoot motion collection unit, and the lower shank motion collection unit, said detachable processing unit for processing data from said accelerometers and said plurality of sensors; and g) a visual display unit in electrical communication with the detachable processing unit for displaying the data processed by the processing unit.

12. The portable human gait analysis apparatus of claim 11, wherein the data from the central processing unit passes through an I/O unit to a telemetry unit for transfer to at least one of a PC and PDA, for storage and further analysis.

13. The portable human gait apparatus of claim 12, wherein the data from the telemetry unit is transferred to at least one of: a walkman, a TV, a VCR, a DVD player, a CD player, a projection unit, a game console, a stereo and an internet site for entertainment purposes.

14. The portable human gait analysis apparatus of claim 11, wherein the plantar pressure collection unit positions force sensor resistors and pressure sensors along a first phalange, a second phalange, a third phalange, a fourth phalange in the forefoot, along a first metatarsal head, a second metatarsal head, and a fourth metatarsal head in the forefoot, along a first metatarsal base, a fourth metatarsal base and a fifth metatarsal base in the midfoot, underneath a distal portion of a medial and lateral side of a calcaneus in the midfoot, and at the medial and lateral surfaces of the calcaneus in the rearfoot, to provide accurate measurement of maximum pressure, mean pressure, and the center of pressure line.

15. The portable human gait analysis apparatus of claim 11 wherein the information displayed on the processing and display unit comprises vital gait information, including over-pronate, supinate, and neutral plantar pressure distribution and the amount of eversion/inversion angle.

16. The portable human gait analysis apparatus of claim 11, wherein the processing and display unit provides a color coded mapping data, which has been normalized by body weight calibration.

17. The portable human gait analysis apparatus of claim 11, wherein said soft casing unit is sized to fit within a user's shoe, with the rearfoot motion collection unit, the lower shank motion unit, and the processing and display unit attached to the outer portion of the user's shoe.

18. The portable human gait analysis apparatus of claim 11, wherein independent measurements are taken for said user's right foot and left foot, and said processing and display units function independently of each foot.

19. The portable human gait analysis apparatus of claim 11, wherein past and current data is stored in memory, and processed by the central processing unit for comparison between use.

20. The portable human gait analysis apparatus of claim 11, wherein the display unit is a LCD display unit.

21. A portable human gait analysis apparatus for releasable securement about a user's foot, wherein the apparatus comprises:

a) a detachable sole which is flexible, durable, electrically insulating, and resilient;

b) a soft casing unit having a detachable sole cover, a detachable foot cover, a detachable shank cover, and a releasable securement means for releasably and adjustably securing the detachable sole cover, the detachable foot cover, and the detachable shank cover about said user's foot;

c) a plantar pressure collection unit positioned between a plantar side of said user's foot and the detachable sole, to identify the center of pressure line and excessive and abnormal loads on the sole of the foot;

d) a rearfoot motion collection unit having at least one accelerometer sensor and a plurality of rate sensors to calculate rearfoot kinematic data crucial to identify the motions of pronation and supination;

e) a lower shank motion collection unit having at least one accelerometer sensor and a plurality of rate sensors to provide lower shank motion data, which when combined with data from the rearfoot kinematic data, provides three dimensional static and dynamic acceleration, angular velocity, 2-axis tilt information, and static and dynamic foot movements;

f) a detachable processing unit in electrical communication with the plantar pressure collection unit, the rearfoot motion collection unit, and the lower shank motion collection unit, said detachable processing unit for processing data from said accelerometers and said plurality of sensors, which has been normalized by body weight and calibration; and g) an LCD visual display unit in electrical communication with the detachable processing unit for displaying the data comprises vital gait information, including over-pronate, supinate, and neutral plantar pressure/distribution and the amount of eversion/inversion angle of the user's foot.

22. The portable human gait analysis apparatus of claim 21, wherein the plantar pressure collection unit positions force sensor resistors and pressure sensors along a first phalange, a second phalange, a third phalange, a fourth phalange in the forefoot, along a first metatarsal head, a second metatarsal head, and a fourth metatarsal head in the forefoot, along a first metatarsal base, a fourth metatarsal base and a fifth metatarsal base in the midfoot, underneath a distal portion of a medial and a lateral side of a calcaneus in the midfoot, and at the medial and lateral surfaces of the calcaneus in the rearfoot, to provide accurate measurement of maximum pressure, mean pressure, and pressure line.

23. The portable human gait analysis of claim 21, wherein independent measurements are taken for said user's right foot and left foot, and said processing and display units function independently for each foot.

24. A portable human gait analysis apparatus for releasable securement about a user's foot, wherein the apparatus comprises: a detachable sole which is flexible, durable, electrically insulating, and resilient, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a plantar pressure collection unit positioned between a plantar side of the user's foot and the detachable sole, to identify the center of pressure line and excessive and abnormal loads on the sole of the foot, a detachable processing unit in electrical communication with the plantar pressure collection unit, said detachable processing unit for processing data from said plantar pressure collection unit, said data being normalized by body weight calibration, and an LCD visual display unit in electrical communication with the detachable processing unit for displaying the data processed by the processing unit, and the information displayed comprising vital gait information comprising over-pronate, supinate, and neutral plantar pressure/distribution and the amount of eversion/inversion angle of the user's foot.

25. The portable human gait analysis apparatus of claim 24 further comprising a rearfoot motion collection unit having at least one accelerometer sensor and a plurality of rate sensors to calculate rearfoot kinematic data crucial to identify the motions of pronation and supination, said detachable processing unit further being in electrical communication with the rearfoot motion collection unit and being further configured for processing said rearfoot kinematic data from said at least one accelerometer sensor and said plurality of rate sensors, said rearfoot kinematic data further being normalized by body weight calibration.

26. The portable human gait analysis apparatus of claim 24 further comprising a lower shank motion collection unit having at least one accelerometer sensor and a plurality of rate sensors to provide lower shank motion data, said detachable processing unit further being in electrical communication with the lower shank motion collection unit and further configured for processing said lower shank motion data from said at least one accelerometer sensor and said plurality of rate sensors, said lower shank motion data further being normalized by body weight calibration.

27. A portable human gait analysis apparatus for releasable securement about a user's foot, wherein the apparatus comprises: a detachable sole, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a rearfoot motion collection unit having at least one accelerometer sensor and at least one rate sensor, a detachable processing unit in electrical communication with the rearfoot motion collection unit, said detachable processing unit being configured for processing data from said at least one accelerometer sensor and said at least one rate sensor, and a visual display unit in electrical communication with the detachable processing unit for displaying the data processed by the processing unit.

28. The portable human gait analysis apparatus of claim 27 further comprising a lower shank motion collection unit having at least one accelerometer sensor and at least one rate sensor, said detachable processing unit being further in electrical communication with said lower shank motion collection unit and being further configured for processing data from said at least one accelerometer sensor and said at least one rate sensor of said lower shank motion collection unit.

29. A portable human gait analysis apparatus for releasable securement about a user's foot, wherein the apparatus comprises: a detachable sole which is flexible, durable, electrically insulating, and resilient, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a plantar pressure collection unit positioned between a plantar side of said user's foot and the detachable sole, to identify the center of pressure line and excessive and abnormal loads on the sole of the foot, a detachable processing unit in electrical communication with the plantar pressure collection unit, said detachable processing unit being configured for processing data from said plantar pressure collection unit, and a visual display unit in electrical communication with the detachable processing unit for displaying the data processed by the processing unit, a rearfoot motion collection unit having at least one accelerometer sensor and a plurality of rate sensors to calculate rearfoot kinematic data crucial to identify the motions of pronation and supination, said detachable processing unit further being in electrical communication with the rearfoot motion collection unit, said detachable processing unit being further configured for processing data from said at least one accelerometer sensor and said plurality of rate sensors.

30. The portable human gait analysis apparatus of claim 29 further comprising a lower shank motion collection unit having at least one accelerometer sensor and a plurality of rate sensors to provide lower shank motion data, said detachable processing unit further being in electrical communication with the lower shank motion collection unit and further being configured for processing said lower shank motion data from said at least one accelerometer sensor and said plurality of rate sensors.

31. A portable human gait analysis apparatus for releasable securement about a user's foot, wherein the apparatus comprises: a detachable sole which is flexible, durable, electrically insulating, and resilient, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a rearfoot motion collection unit having at least one accelerometer sensor and a plurality of rate sensors to calculate rearfoot kinematic data crucial to identify the motions of pronation and supination, a detachable processing unit in electrical communication with the rearfoot motion collection unit, said detachable processing unit being configured for processing said rearfoot kinematic data from said at least one accelerometer sensor and said plurality of rate sensors, and a visual display unit in electrical communication with the detachable processing unit for displaying the data processed by the processing unit.

32. The portable human gait analysis apparatus of claim 31 further comprising a lower shank motion collection unit having at least one accelerometer sensor and a plurality of rate sensors to provide lower shank motion data, which when combined with data from the rearfoot kinematic data, to provide three dimensional static and dynamic acceleration, angular velocity, 2-axis tilt information, and static and dynamic foot movements, said detachable processing unit further being in electrical communication with the lower shank motion collection unit and configured for processing said lower shank motion data from said at least one accelerometer sensor and said plurality of rate sensors from said lower shank motion collection unit.

33. A portable human gait analysis apparatus for releasable securement about a user's foot, wherein the apparatus comprises: a detachable sole which is flexible, durable, electrically insulating, and resilient, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a rearfoot motion collection unit having at least one accelerometer sensor and a plurality of rate sensors to calculate rearfoot kinematic data crucial to identify the motions of pronation and supination, a detachable processing unit in electrical communication with the rearfoot motion collection unit, said detachable processing unit configured for processing said rearfoot kinematic data from said at least one accelerometer sensor and said plurality of rate sensors, which have been normalized by body weight calibration, and an LCD visual display unit in electrical communication with the detachable processing unit for displaying the data processed by the processing unit, and the information displayed comprising vital gait information comprising over-pronate, supinate, and neutral plantar pressure/distribution and the amount of eversion/inversion angle of the user's foot.

34. The portable human gait analysis apparatus of claim 33 further comprising a lower shank motion collection unit having at least one accelerometer sensor and a plurality of rate sensors to provide lower shank motion data, which when combined with data from the rearfoot kinematic data, provides three dimensional static and dynamic acceleration, angular velocity, 2-axis tilt information, and static and dynamic foot movements, said detachable processing unit further being in electrical communication with the lower shank motion collection unit and further configured for processing said lower shank motion data from said at least one accelerometer sensor and said plurality of rate sensors of said lower shank motion collection unit, which have been further normalized by body weight calibration.

35. A portable human gait analysis apparatus for releasable securement about a user's foot, wherein the apparatus comprises: a detachable sole, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a plantar pressure collection unit positioned between a plantar side of said user's foot and the detachable sole, a rearfoot motion collection unit having at least one accelerometer sensor and at least one rate sensor, a detachable processing unit in electrical communication with the plantar pressure collection unit, said detachable processing unit being configured for processing data from the plantar pressure collection unit, said detachable processing unit further being in electrical communication with said rearfoot motion collection unit, said processing unit being further configured for processing data from at least one accelerometer sensor and said at least one rate sensor, and a visual display unit in electrical communication with the detachable processing unit for displaying the data processed by the processing unit.

36. The portable human gait analysis apparatus of claim 35 further comprising a lower shank motion collection unit having at least one accelerometer sensor and at least one rate sensor, said detachable processing unit further being in electrical communication with said lower shank collection unit and further being configured for processing data from said at least one accelerometer sensor and said at least one rate senor.

37. A portable human gait analysis apparatus for releasable securement about a user's foot, wherein the apparatus comprises: a detachable sole, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a lower shank motion collection unit having at least one accelerometer senor and at least one rate senor, a detachable processing unit in electrical communication with the lower shank motion collection unit, said detachable processing unit being configured for processing data from said at least one accelerometer and said at least one rate senor, and a visual display unit in electrical communication with the detachable processing unit for displaying the data processed by the processing unit.

38. A portable human gait analysis apparatus for releasable securement about a user's foot, wherein the apparatus comprises: a detachable sole which is flexible, durable, electrically insulating, and resilient, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a lower shank motion collection unit having at least one accelerometer sensor and a plurality of rate sensors to provide lower shank motion data, a detachable processing unit in electrical communication with the lower shank motion collection unit, said detachable processing unit being configured for processing said lower shank motion data from said at least one accelerometer sensor and said plurality of rate sensors, and a visual display unit in electrical communication with the detachable processing unit for displaying the data processed by the processing unit.

39. A portable human gait analysis apparatus for releasable securement about the user's foot, wherein the apparatus comprises: a detachable sole which is flexible, durable, electrically insulating, and resilient, a soft casing unit having a detachable sole cover, a detachable foot cover, a detachable shank over, and a releasable securement means for releasably and adjustably securing the detachable sole cover, the detachable foot cover, and the detachable shank cover about said user's foot, a lower shank motion collection unit having at least one accelerometer sensor and a plurality of rate sensors to provide lower shank motion data, a detachable processing unit in electrical communication within the lower shank motion collection unit, said detachable processing unit being configured for processing said lower shank motion data from said at least one accelerometer sensor and said plurality of rate sensors, which have been normalized by body weight calibration, and an LCD visual display unit in electrical communication with the detachable processing unit for displaying the data processed by the processing unit, and the information displayed comprising over-pronate, supinate, and neutral plantar pressure/distribution and the amount of eversion/inversion angle of the user's foot.

40. A portable human gait analysis apparatus for releasable securement about a user's foot, wherein the apparatus comprises: a detachable sole, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a plantar pressure collection unit positioned between a plantar side of said user's foot and the detachable sole, said plantar pressure collection unit having four sensor resistors and pressure sensors along a first phalange, a second phalange, a third phalange, a fourth phalange in the forefoot, along a first metatarsal head, a second metatarsal head and a fourth metatarsal head in the forefoot, along a first metatarsal base, a fourth metatarsal base and a fifth metatarsal base in the midfoot, underneath a distal portion of a medial and lateral side of a calcaneus in the midfoot, and at the medial and lateral surfaces of a calcaneus in the rearfoot, to provide accurate measurement of maximum pressure, mean pressure, and the center of pressure line, a detachable processing unit in electrical communication with the plantar pressure collection unit, said detachable processing unit being configured for processing data from the plantar pressure collection unit, and a visual display unit in electrical communication with the detachable processing unit for displaying the data processed by the processing unit.

41. A portable human gait analysis apparatus for releasable securement about a user's foot, wherein the apparatus comprises: a detachable sole which is flexible, durable, electrically insulating, and resilient, a soft casing unit having a detachable sole cover, a detachable foot cover, a detachable shank cover, and a releasable securement means for releasably and adjustably securing the detachable sole cover, the detachable foot cover, and the detachable shank cover about said user's foot, a plantar pressure collection unit positioned between a plantar side of said user's foot and the detachable sole, to identify the center of pressure line and excessive and abnormal loads on the sole of the foot, said plantar pressure collection unit having four sensor resistors and pressure sensors along a first phalange, a second phalange, a third phalange, a fourth phalange in the forefoot, along a first metatarsal head, a second metatarsal head and a fourth metatarsal head in the forefoot, along a first metatarsal base, a fourth metatarsal base and a fifth metatarsal base in the midfoot, underneath a distal portion of a medial and lateral side of a calcaneus in the midfoot, and at the medial and lateral surfaces of a calcaneus in the rearfoot, to provide accurate measurement of maximum pressure, mean pressure, and the center of pressure line, a detachable processing unit in electrical communication with the plantar pressure collection unit, said detachable processing unit being configured for processing data from said plantar pressure collection unit, and a visual display unit in electrical communication with the detachable processing unit for displaying the data processed by the processing unit.

* * * * *